United States Patent [19]

George

[11] 4,167,464

[45] Sep. 11, 1979

[54] PHOTOPOLYMERIZED HYDROPHILIC INTERPOLYMERS OF UNSATURATED CARBOXYLIC ACID AND ESTERS

[75] Inventor: Paul J. George, Richfield, Ohio

[73] Assignee: The B. F. Goodrich Company, Akron, Ohio

[21] Appl. No.: 951,906

[22] Filed: Oct. 16, 1978

[51] Int. Cl.$^2$ .............................. C08F 2/46; C08F 4/00
[52] U.S. Cl. ......................... 204/159.23; 204/159.12; 204/159.13; 204/159.14; 204/159.24; 260/17.4 SG; 526/240; 526/292; 526/293; 526/312; 526/278; 526/923
[58] Field of Search ...................... 204/159.12, 159.13, 204/159.23, 159.24, 159.14; 526/240, 292, 923, 312, 278

[56] References Cited

U.S. PATENT DOCUMENTS

| | | | |
|---|---|---|---|
| 3,915,921 | 10/1975 | Schlatzer | 260/17.4 SG |
| 3,966,573 | 6/1976 | Bean | 204/159.23 |
| 4,062,817 | 12/1977 | Westermann | 260/17.4 SG |
| 4,066,522 | 1/1978 | Machi et al. | 204/159.24 |
| 4,066,583 | 1/1978 | Spaulding | 260/17.4 SG |
| 4,069,124 | 1/1978 | Marek et al. | 204/159.24 |

*Primary Examiner*—Richard B. Turer
*Attorney, Agent, or Firm*—Nestor W. Shust

[57] ABSTRACT

Highly water absorbent films and fibers are prepared by photopolymerizing an alkaline metal salt of acrylic acid, at least one alkyl acrylate or methacrylate wherein the alkyl group contains 10 to 30 carbon atoms, at least one alkyl acrylate or methacrylate wherein the alkyl group contains 1 to 4 carbon atoms and a photoinitiator. The resulting interpolymers are particularly useful in the preparation of highly absorbent personal hygiene and care products.

11 Claims, No Drawings

PHOTOPOLYMERIZED HYDROPHILIC INTERPOLYMERS OF UNSATURATED CARBOXYLIC ACID AND ESTERS

BACKGROUND OF THE INVENTION

A variety of hydrophilic polymers which are useful in the manufacture of water absorbent films and fibers have been reported in the prior art. U.S. Pat. No. 3,915,921 discloses copolymers of unsaturated carboxylic acid monomers with alkyl acrylate esters wherein the alkyl group contains 10 to 30 carbon atoms. However, because of the high Tg of these polymeric materials, it is difficult to extrude them in fiber of film form. Furthermore, films pressed from the powders require high temperatures, the films are brittle and fragile, and have a reduced initial rate of water absorption.

U.S. Pat. No. 4,062,817 discloses polymers of unsaturated copolymerizable carboxylic acids, at least one alkyl acrylate or methacrylate wherein the alkyl group has 10 to 30 carbon atoms and another alkyl acrylate or methacrylate wherein the alkyl group has 1 to 8 carbons. This composition alleviated many of the deficiencies of the earlier compositions. Further improvements in the hydrophilic properties were obtained by compositions disclosed in U.S. Pat. No. 4,066,583. This patent discloses a composition comprising (1) a copolymer of the type disclosed in the '817 patent, except that after copolymerization 30 to 90 percent of the carboxylic groups were neutralized with an alkali metal or ammonia and (2) an aliphatic glycol, a plasticizer which is important in facilitating extrusion of the polymer.

SUMMARY OF THE INVENTION

An interpolymer is prepared by photopolymerizing 50 to 90 weight percent of acrylic acid, 60 to 100% of the carboxylic groups of said acid having been neutralized prior to polymerization with an alkaline metal hydroxide, 2 to 20 weight percent of an alkyl acrylate or methacrylate wherein the alkyl group has 10 to 30 carbon atoms, 5 to 30 weight percent of an alkyl acrylate wherein the alkyl group has 1 to 9 carbon atoms and a photoinitiator. After spreading the monomer mixture to the desired thickness or after spinning it into a fiber it is polymerized upon exposure to a UV light source. The resulting film or fibers have extremely rapid and high degree of absorption of water and body fluids, such as urine or blood.

DETAILED DISCLOSURE

This invention is directed to a photopolymerized interpolymer which has outstanding absorption and retention properties of water and ionic solutions such as urine or blood. The interpolymer is prepared from a monomer mixture comprising (a) 50 to 90 weight percent of acrylic acid, 70 to 100 percent and most preferably 80 to 100 percent of the carboxylic groups having been neutralized with an alkali metal hydroxide or ammonia base prior to polymerization, (b) 2 to 25 weight percent of a higher acrylic ester monomer of the formula

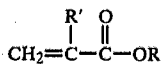

wherein R' is hydrogen, methyl or ethyl and R is an alkyl group of 10 to 30 carbon atoms, (c) 5 to 30 weight percent of a lower acrylic ester monomer of the formula

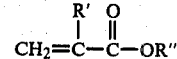

wherein R" is a lower alkyl group having 1 to 8 carbon atoms, 0 to 50 percent of said lower acrylic ester being replaced by acrylic or methacrylic nitrile or amide, and (d) 0.01 to 5 weight percent of a photoinitiator.

The higher acrylic ester monomers are those which have a long chain aliphatic group and may be represented by the formula

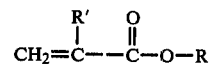

wherein R is an alkyl group having from 10 to 30 carbon atoms, preferably 10 to 18 carbon atoms and R' is hydrogen, methyl or ethyl group. Representative higher alkyl acrylic esters are decyl acrylate, isodecyl acrylate, lauryl acrylate, stearyl acrylate, behenyl acrylate and melissyl acrylate and the corresponding alkacrylates including methacrylates for example. Mixtures of two or three or more long chain acrylic esters may be successfully polymerized with one of the carboxylic monomers to provide useful thickening resins of this invention. Particularly useful are those acrylates and methacrylates where the alkyl group contains 10 to 18 carbon atoms present preferably in amounts of about 5 to 20 weight percent of the total monomers. Outstanding polymers have been made with 15±5 weight percent isodecyl methacrylate, 10±3 weight percent lauryl methacrylate, 7±3 weight percent stearyl methacrylate.

The lower acrylic esters can be represented by the formula

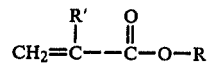

wherein R is an alkyl, alkoxy, haloalkyl, cyanoalkyl, hydroxyalkyl and like groups having from 1 to 8 carbon atoms and R' is hydrogen, methyl or ethyl group. Preferably R' is hydrogen or methyl and R is alkyl, most preferably methyl, and the lower ester is present in the amount of from 5 to 20 and most preferably 7 to 17 weight percent.

Representative acrylates include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethyl-hexyl acrylate, nonyl acrylate, hexyl acrylate, n-hexyl methacrylate, hydroxy ethyl methacrylate, dimethylamino ethylmethacrylate.

In addition to the above discussed monomers from which the copolymers of this invention are prepared, minor amounts, that is less than 5 weight percent of additional monomers may also be used. Whether these additional monomers are employed will depend on the end use and the physical properties required, that is, the speed and degree of absorption and the tear strength needed for the film or fabric. Such additional monomers are discussed below.

One type of such additional monomers are α,β-olefinically unsaturated nitriles preferably the monoolefinically unsaturated nitriles having from 3 to 10 carbon atoms such as acrylonitrile, methacrylonitrile, ethacrylonitrile, chloroacrylonitrile, and the like. Most preferred nitriles are acrylonitriles and methacrylonitrile.

Another useful class of additional monomers which may be incorporated in the interpolymers of this invention is monoethylenically unsaturated amides which have at least one hydrogen on the amide nitrogen and the olefinic unsaturation is alphabeta to the carbonyl group. The preferred amides have the structure

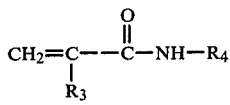

wherein $R_3$ is a member of the group consisting of hydrogen and an alkyl group having from 1 to 4 carbon atoms and $R_4$ is a member of the group consisting of hydrogen and an alkyl group having from 1 to 6 carbon atoms. Representative amides include acrylamide, methacrylamide, N-methyl acrylamide, N-t-butyl acrylamide, N-cyclohexyl acrylamide, N-ethyl acrylamide and others. Of the amides most preferred are acrylamide and methacrylamide.

Other acrylic amides include N-alkylol amides of alpha,beta-olefinically unsaturated carboxylic acids including those having from 4 to 10 carbon atoms such as N-methylol acrylamide, N-ethanol acrylamide, N-propanol acrylamide, and the like. The preferred monomers of the N-alkylol amide type are the N-alkylol amides of alpha, beta-monoolefinically unsaturated monocarboxylic acids and the most preferred is N-methylol acrylamide.

Also useful are N-alkoxymethyl acrylamides which have the structure

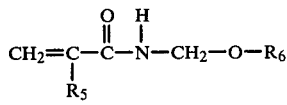

wherein $R_5$ is selected from the group consisting of hydrogen and methyl, and $R_6$ is an alkyl group having from 1 to 8 carbon atoms. It is thus intended that where references are made herein regarding the essential N-substituted alkoxymethyl amides, the term "acrylamide" includes "methacrylamide" within its meaning. The preferred alkoxymethyl acrylamides are those wherein $R_6$ is an alkyl group containing from 2 to 5 carbon atoms, and especially useful is N-butoxymethyl acrylamide.

The above discusses monomers are copolymerized by subjecting the monomer mixture to UV light. If a film is desired the monomer can be spread on a surface to the desired thickness, e.g. 1 mil to 25 mil, and then subjected to UV light for a short time. e.g. 1 second to several minutes. The actual length of irradiation will depend on a number of factors, such as the thickness of the monomer film, the distance from and the intensity of the source of irradiation, the specific monomers employed and the ratio of such monomers to each other, the presence or absence of additional comonomers and the nature and the amount of the photoinitiator employed. The type of photoinitiator employed will depend at least in part on the type of UV irradiation employed (particularly its wave length) since various photoinitiators may be decomposed by UV light of different wavelengths). If it is desired that the material be in the form of fibers, the monomer mixture can be thickened and then spun into fibers which, upon exposure to UV light, are polymerized.

In order to effect quick and efficient polymerization under UV light, 0.01 to 5 weight percent of a photoinitiator, preferably 0.1 to 5 percent and more preferably 0.3 to 1.0 weight percent, must be incorporated into the monomer mixture. Any compound which dissociates into free radicals when exposed to UV radiation can be employed. There are many known photoinitiators or photosensitizers such as acetophenone, propiophenone, benzophenone, xanthone, fluorenone, benzaldehyde, fluorene, anthraquinone, triphenylamine, carbazole, 3- or 4-methylaceto-phenone, 3- or 4-pentylacetophenone, 3- or 4-methoxyacetophenone, 3- or 4-bromoacetophenone, 3- or 4-allylacetophenone, p-diacetylbenzene, 3- or 4-methoxybenzophenone, 3- or 4-methylbenzophenone, 3- or 4-chlorobenzophenone, 4,4-dimethoxybenzophenone, 4-chloro-4'-benzylbenzophenone, 3-chloroxanthone, 3,9-dichloroxanthone, 3-chloro-8-nonyl-xanthone, 3-methoxyxanthone, 3-iodo-7-methoxyxanthone, 2,2-dimethoxyacetophenone, 2,2-dimethoxy-2-phenylacetophenone, 2,2-diethoxyacetophenone, 2,2-dibutoxyacetophenone, 2,2-dihexoxyacetophenone, 2,2-di(2-ethylhexoxy)acetophenone, 2,2-diphenoxyacetophenone, benzoin, methyl benzoin ether, ethyl benzoin ether, isopropyl benzoin ether, butyl benzoin ether, isobutyl benzoin ether, benzoin acetate, benzoin phenyl carbamate, α,α-diethoxyacetophenone, α,α-diethoxy-a-phenylacetophenone, α,α-dimethoxy-a-phenylacetophenone, 4,4'-dicarboethoxybenzoin ethyl ether, α-chloroacetophenone, α-bromoacetophenone, benzoin phenyl ether, α-methylbenzoin ethyl ether, benzoin acrylate, α-methylolbenzoin methyl ether, α,α,α-trichloroacetophenone, o-bromoacetophenone, 4-(benzolyphenylmethoxycarbonylimino)-2-(acrylyloxyethoxycarbonylimino)-1-methylbenzene, cumene hydroperoxide, benzoyl peroxide, dicumyl peroxide, tertbutyl perbenzoate, α,α-azobisisobutyronitrile, phenyl disulfide, chlorOmethylbenzanthrone, chloromethylanthraquinone, chloromethylnaphthalene, bromomethylbenzanthrone, bromomethylanthraquinone, bromomethylnaphthalene, and the like.

In addition to the photoinitiator it may be advantageous to employ also from 0.3 to 5.0 percent of an air cure promoter. Illustrative examples of air cure promoters are anthraquinone, thioxanthone, 2-benzoylpyridine, 4-chlorobenzophenone, 4-methoxybenzophenone, 4-methylbenzophenone, benzophenone, 2-chloroanthraquinone, dibenzosuberone, o-benzoylbenzophenone, chlorinated terphenyls, mercaptoacetic acid, mercaptoethanol, and the like.

The monomer mixtures are prepared as aqueous dispersions which eliminates the need for organic solvents. This avoids the pollution problems caused by the removal of organic solvents or the cost associated with the removal of the pollutants. In order to obtain a stable homogeneous dispersion of the monomers, it is preferred that the aqueous dispersions contain 0.01 to 5%, and preferably 0.1 to 1%, of a surface active agent such as an anionic, amphoteric, or nonionic dispersing agent or a mixture of dispersants. Useful anionic dispersing agents include alkali metal or ammonium salts of the sulfates of alcohols having from 8 to 18 carbon atoms such as sodium lauryl sulfate; ethanolamine lauryl sulfate, ethylamine lauryl sulfate; alkali metal and ammonium salts of sulfonated petroleum and paraffin oils; sodium salts of aromatic sulfonic acids such as dodecane-1-sulfonic acid and octadecane-1-sulfonic acid; aralkyl sulfonates such as sodium isopropyl benzene sulfonate, sodium dodecyl benzene sulfonate and sodium isobutyl naphthalene sulfonate; alkali metal and ammonium salts of sulfonated dicarboxylic acid esters such as sodium dioctyl sulfosuccinate, disodium-n-octadecyl sulfosuccinate; alkali metal or ammonium salts of free acid of complex organic mono-and diphosphate esters, sulfosuccinic acid derivatives (AEROSOL dispersants), organic phosphate esters (GAFAC dispersants) and the like. Nonionic dispersants such as octyl-or nonylphenyl polyethoxyethanol as well as the PLURONIC and the TRITON dispersants may also be used. Also useful are amphoteric dispersants such as dicarboxylic coconut derivatives (MIRANOL). Further examples of useful dispersants are those disclosed beginning on page 102 in J. Van Alphen's "Rubber Chemicals", Elsevier Publishing Co., 1956.

The compositions of this invention do not require additional materials, such as for example plasticizers to enable the manufacture of thin films. However materials such as glycols may be advantageously incorporated into the present compositions to improve the wicking property of films and fibers. Wicking is the ability of the liquid to move along the fibers or the film and therefore affects the speed with which the liquid is absorbed. Glycols that are useful for that purpose are diols containing 2 to 10, preferably 2 to 8, carbon atoms such as ethylene glycol, propylene glycol, butylene glycol, diethylene glycol, triethylene glycol and tetraethylene glycol. Other glycols that have been used include 1,3-butanediol, 1,5-pentanediol, 1,6-hexanediol and alkyl-substituted derivatives such as 2,2-dimethyl-1,3-propanediol, 2,2-diethyl-1,3-propanediol, 2-ethyl-2-methyl-1,3-propanediol, 2-methyl-2,4-pentanediol, 2,5-dimethyl-2,5-hexanediol, 2-ethyl-1,3-hexanediol, and the like. Also useful are glycol ethers including diethylene glycol, triethylene glycol, tetraethylene glycol and polyethylene glycols of the formula HO(CH$_2$CH$_2$O)$_n$H wherein n is an integer, for example, greater than 5 and while it may be as great as 50 or more, better results are generally obtained when the molecular weight of the polyethylene glycol is below about 400. Other glycol ethers include dipropylene glycol, tripropylene glycol and polypropylene glycol of the formula

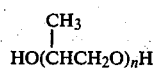

where n is an integer, for example, greater than 5 and while it may be as great as 50 or more, better results are generally obtained when the molecular weight of the polypropylene glycol is below about 400, and monoalkyl ethers of these glycols, for example, ethylene glycol monomethyl ether, ethylene glycol monobutyl ether, diethylene glycol monoethyl ether, triethylene glycol monobutyl ether, tetraethylene glycol monoethyl ether, tripropylene glycol monomethyl ether, and the like. Polyhydroxy compounds containing more than two hydroxy groups may be used in conjunction with the glycols set forth above in amounts of no greater than about 50 weight percent of the total weight mixture of glycol and polyol. Such materials include, for example, glycerol, trimethylol propane, 2(hydroxymethyl)-2-methyl-1,3-propanediol, 1,2,6-hexanetriol, and the like. Glycols may be used in the amount of from 1 to 10 weight percent of the monomer mixture.

Although cross-linking agents are not required to obtain useful, highly absorbent compositions of this invention, it may be desirable to incorporate a cross-linking agent since films prepared from compositions containing a cross-linking agent tend to have greater gel strength and an improved ability for the copolymers to swell under a confining pressure. Cross-linking agents may be used in the concentration of about 0 to about 15% by weight based on the total weight of the monomers, and preferably about 1 to about 10%.

Useful cross-linking monomers are polyalkenyl polyether having more than one alkenyl ether grouping per molecule. The most useful possess alkenyl groups in which an olefinic double bond is attached to a terminal methylene group, CH$_2$=C<. Other crosslinking monomers include for example, diallyl esters, dimethallyl ethers, allyl or methallyl acrylates and acrylamides, tetraallyl tin, tetravinyl silane, polyalkenyl methanes, diacrylates and dimethacrylates, divinyl compounds as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, pentaerythritol triacrylate, tetramethylene dimethyacrylate, tetramethylene diacrylate, ethylene diacrylate, ethylene dimethacrylate, triethylene glycol dimethacrylate, and the like.

The copolymers of this invention can be photopolymerized in a film or a fiber form. The resulting film or fiber is an elastic, flexible material that has an appreciable degree of strength. If a fine, flaky form is desired, the film can be converted to such a form by drying and then pulverizing or grinding it in standard equipment.

As water absorbent materials these polymers find many uses in film, fiber, fabric and similar forms. They are of particular utility in the disposable nonwoven industry where there is need for polymers which will absorb and retain water and ionic physiological fluids. An important feature of these polymers is their enhanced thickening property even in the presence of a salt. Specific applications include disposable diapers, medical-surgical supplies and personal care products. Such applications require a polymer which must imbibe the liquid to be absorbed rapidly and be a polymer that will not dissolve. Further, the fluid must be immobilized or congealed in some way to be retained. The materials may also be used as suitable additives to greatly increase the absorptive power of conventional absorbents such as cotton, wood pulp and other cellulosic absorbents used in applications such as wiping cloths, surgical sponges, catamenial devices, and the like. In a specific application, for example, a disposable diaper, there is an inner layer of a soft absorbent nonwoven material that absorbs and passes urine to an inner layer of fluffy fibrous absorbent material, wherein during the construction of this nonwoven fiber agglomerates or fibers of the polymers of this invention may be included and an additional impervious plastic layer, as polyethylene. A film of the copolymers of this invention may be used between the outer plastic layer and the inner fluffy absorbent layer. Use of the polymers of this invention can result in reduction in the bulk size of many disposable nonwovens.

The instant copolymers can also be used as flocculants in water treatment, in metallurgical processes, in oare beneficiation and flotation, in agricultural applications such as in soil treatment or seed coating or in any applications where the inherent properties of the polymer are desirable, such as its thickening property in an aqueous medium.

To prepare the cured copolymers of this invention, the monomers, a dispersant and a photoinitiator are mixed in a vessel. Then either a film or fibers are produced from the monomer mixture which, upon exposure to UV light, are rapidly polymerized. The various steps in the procedure are described in greater detail below.

Monomer Mixture Preparation: The monomer mixture can be prepared by following one of two simple procedures. One method is to dissolve a previously prepared and dried alkali metal or ammonium acrylate in water to which is then added a dispersant. To the aqueous solution is then added a mixture of acrylate esters which already contain a photoinitiator. Another method is to prepare the acrylate salt in situ by adding acrylic acid to the proper amount of cold aqueous base (e.g. KOH, NaOH or NH$_4$OH) with cooling. To the aqueous solution is then added a mixture of the acrylate esters to which a photoinitiator was previously added; the dispersant is added last.

Film Preparation: The aqueous monomer dispersion is spread to a desired thickness (e.g. by the use of Boston-Bradley adjustable blade, by spraying or other known means) on a suitable substrate (e.g. Mylar, polyethylene, paper, etc.). The liquid film is then exposed to UV irradiation which polymerizes the monomer mixture into a soft, pliable form. If desired this film can be dried in an oven at about 50° C. for 1 to 15 min. After drying the film may still retain some flexibility or become brittle and flaky, depending on the length of drying.

Fiber Preparation: The aqueous monomer dispersion is thickened to the desired degree with a nonreactive thickening agent such as a cellulose derivative as for example hydroxypropyl cellulose, high molecular weight polyvinyl pyrrolidone and the like; natural gums such as guar gum, locust bean gum, gum tragacanth; agar, naturally occuring hydrocolloids such as alginates and the like. Fibers are then spun from a spinneret in a regular manner and immediately exposed to UV irradiation.

To further illustrate the present invention the following examples are presented in table form below. The copolymers and the films were prepared according to the procedures described above. The examples are presented for illustrative purposes only without any intention to introduce any limitations.

TABLE I

| Example No. | 1 | 2 | 3 | 4 | 5 | 6 |
|---|---|---|---|---|---|---|
| Sodium hydroxide | 43.6g | 43.6g | 46.1g | 43.3g | 34.6g | 32.5g |
| % Neutralization | 95% | 95% | 100% | 100% | 75% | 75% |
| Water | 152.0g | 152.0g | 160.0g | 159.0g | 149.0g | 148.0g |
| Acrylic acid | 83.0g | 78.0g | 83.0g | 78.0g | 83.0g | 78.0g |
| Lauryl methacrylate | 7.0g | 7.0g | 7.0g | 7.0g | 7.0g | 7.0g |
| Methyl methacrylate | 10.0g | 15.0g | 10.0g | 15.0g | 10.0g | 15.0g |
| AEROSOL A102(a) | 1.24g | 1.24g | 1.24g | 1.24g | 1.19g | 1.18g |
| IRGACURE 651(b) | 0.62g | 0.62g | 0.62g | 0.62g | 0.60g | 0.59g |

(a)AEROSOL A102 is disodium ethoxylated alcohol half ester of sulfosuccinic acid, a dispersant.
(b)IRGACURE 651 is 2,2-dimethoxy-2-phenylacetophenone, a photoinitiator.

| Example No. | 7 | 8 | 9 | 10 | 11 | 12 |
|---|---|---|---|---|---|---|
| Sodium hydroxide | 43.6g | 43.6g | — | — | 43.6g | 46.1g |
| Ammonium hydroxide | — | — | 67.6g | 63.5g | — | — |
| % Neutralization | 95% | 95% | 100% | 100% | 95% | 100% |
| Water | 152.0g | 152.0g | 27.2g | 29.2g | 152.0g | 160.0g |
| Acrylic acid | 83.0g | 83.0g | 83.0g | 78.0g | 83.0g | 83.0g |
| Lauryl methacrylate | 7.0g | — | — | — | 7.0g | (4) |
| Stearyl methacrylate | — | 7.0g | 7.0g | 7.0g | — | — |
| Methyl methacrylate | 10.0g | 10.0g | 10.0g | 15.0g | (3) | (5) |
| AEROSOL A102 | 1.24g | 1.24g | 1.24g | 1.24g | 1.24g | 1.24g |
| IRGACURE 651 | — | — | 0.62g | 0.62g | 0.62g | 0.62g |
| Photoinitiator | 1.0g(1) | 0.83g(2) | — | — | — | — |

(1)N,N'-bis(diethylamino)benzophenone (0.5g) and benzophenone (0.5g)
(2)Benzoin ethyl ether
(3)2-Hydroxyethylmethacrylate (10.0g)
(4)Tridecyl acrylate (7.0g)
(5)n-Butyl acrylate (10.0g)

TABLE II

| Example No. | 13 | 14 | 15 | 16 |
|---|---|---|---|---|
| Sodium hydroxide | 43.6 g | 43.6 g | — | 43.6 g |
| Ammonium hydroxide | — | — | 67.6 g | — |
| % Neutralization | 95% | 95% | 100% | 95% |
| Water | 152.0 g | 152.0 g | 27.2 g | 152.0 g |
| Acrylic acid | 83.0 g | 83.0 g | 83.0 g | 78.0 g |
| Higher acrylate | 7.0 g | 7.0 g | 7.0 g | 7.0 g |
| Lower acrylate | 10.0 g | 10.0 g | 10.0 g | 11.5 g |
| AEROSOL A 102 | 1.24 g | 1.24 g | 1.24 g | 1.24 g |
| IRGACURE 651 | — | — | 0.62 g | 0.62 g |
| Photoinitiator | 1.0 g(1) | 0.83 g(2) | — | — |

(1)N,N'-bis(diethylamino)benzophenone (0.5g) and benzophenone (0.5g)
(2)Benzoin ethyl ether
Higher acrylate:
Ex. 13: lauryl methacrylate;
Ex. 14 & 15: stearyl methacrylate
Ex. 16: tridecyl acrylate.
Lower acrylate:
Ex. 13: 2-ethylhexyl acrylate;
Ex. 14: ethyl methacrylate
Ex. 15: cyclohexyl acrylate;
Ex. 16: 10 g. of 2-ethylhexyl acrylate and 1.5 g. of trimethylolpropane triacrylate.

Copolymers having substantially the same properties were obtained when in some of the above compositions potassium hydroxide was employed in place of sodium or ammonium hydroxide, 2,2-diethyoxyacetophenone in place of IRGACURE 651 and an oligomeric surfactant POLYWET KX-3 (from Uniroyal) or TRITON N-111 (monophenoxy polyethoxy ethanol) in place of AEROSOL A102.

A number of tests are available to determine the absorbency of a material. Following are descriptions of several test procedures which were employed in evaluationg absorbency of the compositions of this invention.

Tea-Bag Test—A weighed film sample 5 cm in diameter enclosed in a sewn strip of cheesecloth resembling a tea bag is immersed in a fluid to be absorbed for a period indicated in the table. After withdrawing from the fluid the excess was drained for 15 minutes and weighed. This was repeated as many times as noted in the table. The same procedure was followed with an identical cheesecloth tea-bag assembly without the polymer sample to determine the weight of fluid absorbed by the cheese cloth. This data was used as a blank. From the above obtained data the amount of fluid absorbed by the polymer is determined.

Static Test A weighed film sample is immersed in a test liquid for 10 minutes. It is then removed from the liquid, the excess liquid drained for a few seconds and then shaken lightly several times. The swelled sample is weighed again to determine the weight of liquid absorbed by the polymer.

Flood-Centrifuge Test (FCT)—The film sample is ground to powder, the resulting powder is weighed and suspended in the test fluid and allowed to absorb under freeswell conditions for 30 minutes. The amount of liquid employed is always in excess of the capacity to absorb: 100 ml. of simulated urine is used per 1 gm. of polymer, while 500 ml. of deionized water is used per 0.25 g. of polymer. The vessel is then centrifuged for 30 min. at a known rpm and from this information G values are calculated employing the formula $$G = \left(\frac{\text{rpm} \times 2\pi}{60}\right) \frac{R^2}{980}$$

where rpm is revolutions per minute; R is the radius of the circle followed by the centrifuge.

After centrifuging the contents, the vessel is drained for 10 minutes through a standard mesh screen. For simulated urine, 60 mesh (250 microns) is used, while for deionized water 40 mesh (420 microns) screen is used. Then the screen and its contents are weighed. By subtracting the weight of the clean screen and of the dry polymer the weight of the fluid absorbed is determined.

This test is described in greater detail by Weaver et al, "Highly Absorbent Starch-Based Polymer", Symposium Papers of the International Nonwoven and Disposables Association, presented in Washington, D.C., March 5-6, 1974.

Demand Wettability Test (DWT)—A test diaper is constructed from a 4 inch diameter pad (10.16 cm.) using materials from a commercial diaper. A film prepared from a polymer to be tested for absorbency is placed in the center of the test diaper between two layers of fluff (wood pulp). A diaper without the polymer film is used as a blank. The demand-wettability apparatus is a burette filled with the test fluid and firmly stoppered at the top, with an air bleed on the side, and a delivery orifice on the bottom connected by a flexible tube to the sample holder. The sample holder has an opening in the center which is connected to the flexible tube that leads to the delivery orifice of the burette. The sample holder is level with the air bleed opening in the burette. With this closed-system arrangement the fluid in the flexible tube that comes up to the opening in the sample holder is at zero pressure. Thus when the test diaper is placed on the sample holder over the opening it will absorb the fluid on its own through wicking action. The sample's own absorbent powder will determine the rate and amount of fluid that will be withdrawn from the burette. The amount of fluid withdrawn at any given time can be easily read from the burette calibration. An additional feature is that absorbency can be measured against a range of pressures that can be obtained by placing various weights on top of the test diaper. Such pressures are intended to simulate the pressures applied on a diaper in actual use.

This test is described in greater detail by Lichstein, "Demand Wettability, a New Method for Measuring Absorbency Characteristics of Fabrics", Symposium Papers -INDA Technical Symposium, 1974, pp. 129-142.

Compression Test (CT)—This test is a follow-up test to the Demand-Wettability Test (DWT). After the sample has absorbed the liquid against a lower pressure in a DWTest, it is removed from the DWT apparatus and placed atop a porous filter funnel. The sample is then subjected to 1.5 psi (0.105 kg/cm$^2$) of pressure for 1 minute and the amount of liquid that is squeezed from the sample is measured. Said pressure corresponds to the maximum pressure that is exerted on portions of a diaper when a toddler is picked up or held. This is 10 to 15 times the pressure that the diaper normally would experience. The sample is then weighed to determine the amount of fluid in grams retained per one gram of polymer.

In Table II below is presented data comparing the abosrbency properties of the copolymer of this invention with two other polymers. Copolymer A corresponds to the copolymers of Example 1 containing 83% of acrylic acid, 7% of lauryl methacrylate and 10% of methyl methacrylate. It was prepared according to the procedure described above, having been photopolymerized in the form of a film. Copolymer B has the same composition as Copolymer A, but was prepared according to the procedure of Example I in U.S. Pat. No. 4,062,817. Copolymer C is a starch graft copolymer SGP-1200 obtained from the U.S. Department of Agriculture. The starch graft copolymer is presently being developed for superabsorbent applications. The absorbency tests reported in Table II below were carried out with simulated urine which had the following compositions: 97.09% distilled water, 1.94% urea, 0.80% sodium chloride, 0.11% magnesium sulfate heptahydrate and 0.06% calcium chloride. The values expressed in the Table are grams or milliliters of liquid (as indicated) absorbed per one gram of the copolymer.

TABLE III

| | Comparative Absorbency Tests | | | |
|---|---|---|---|---|
| Polymer | Tea-Bag (g/g) (ml/g) | DWT (g/g) | CT (g/g) | FCT |
| A | 36 | 36 | 32 | 65 |
| B | 35–40 | 29 | 25–29 | 50–55 |
| C | — | 19 | 24 | 35–40 |

I claim:
1. An interpolymer prepared by photopolymerization of:
(a) 50 to 90 weight percent of acrylic acid, 70 to 100% of the carboxylic groups having been neu- tralized with an alkali metal or ammonium base prior to polymerization.

(b) 2 to 25 weight percent of a higher acrylic ester monomer of the formula

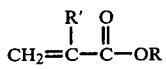

wherein R' is hydrogen, methyl or ethyl and R is an alkyl group of 10 to 30 carbon atoms, (c) 5 to 30 weight percent of a lower acrylic ester monomer of the formula

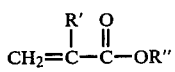

wherein R" is a lower alkyl group having 1 to 8 carbon atoms, 0 to 50 percent of said lower acrylic ester being replaced by acrylic or methacrylic nitrile or amide, and (d) 0.01 to 5 weight percent of a photoinitiator.

2. A composition of claim 1 containing additionally 0.1 to 5 percent of a dispersant.

3. An interpolymer of claim 2, wherein
(a) acrylic acid is in the amount of from 65 to 85 weight percent,
(b) the higher acrylic ester is an acrylate or methacrylate wherein R is an alkyl group of 16 to 21 carbon atoms, said ester being in the amount of from 5 to 20 percent,
(c) the lower acrylic ester is an alkyl acrylate or methacrylate which is in the amount of from 5 to 20 percent,
(d) the photoinitiator is in the amount of from 0.3 to 1.0 percent, and
(e) the dispersant is in the amount of from 0.1 to 1 percent.

4. An interpolymer of claim 3 wherein
(b) the higher acrylic ester is selected from lauryl or stearyl acrylate or methacrylate, and
(c) the lower acrylic ester is methyl acrylate or methacrylate.

5. An interpolymer of claim 3 wherein the photoinitiator is
2,2-dimethoxy-2-phenylacetophenone, N,N'-bis(diethylamino)bgenzophenone, benzophenone, benzoin ethyl ether, or a mixture thereof.

6. An interpolymer of claim 1 prepared from
(a) 83 weight percent of acrylic acid, 80 to 100% of the carboxylic groups having been neutralized,
(b) 7 weight percent of lauryl or stearyl methacrylate, or tridecyl acrylate,
(c) 10 weight percent of methyl acrylate or methacrylate,
(d) 0.3 to 1.0 weight percent of 2,2-dimethoxy 2-phenylacetophenone, N,N'-bis(diethylamino)benzophenone, benzophenone or benzoin ethyl ether, and benzophenone or benzoin ethyl ether, and
(e) 0.1 to 0.3 weight percent of a dispersant.

7. An interpolymer of claim 1 prepared from
(a) 78 weight percent of acrylic acid, 80 to 100% of the carboxylic groups having been neutralized,
(b) 7 weight percent of lauryl or stearyl methacrylate or tridecyl acrylate,
(c) 15 weight percent of methyl acrylate or methyl methacrylate,
(d) 0.3 to 1.0 weight percent of 2,2-dimethoxy 2-phenylacetophenone, N,N'-bis(diethylamino)benzophenone, benzophenone or benzoin ethyl ether, and
(e) 0.1 to 0.3 weight percent of a dispersant.

8. An interpolymer of claim 1 or 3 containing additionally up to 15 weight percent of a cross-linking agent.

9. An interpolymer of claim 1 in the form of a film which is highly absorbent of aqueous liquids.

10. An interpolymer of claim 1 in the form of a fiber which is highly absorbent of aqueous liquids.

11. An article of manufacture designed for absorbing body fluids comprising an absorbent cellulose material and a polymer of claim 1 in the form of a film or fibers.

* * * * *